United States Patent
Kipfer et al.

(10) Patent No.: US 6,368,314 B1
(45) Date of Patent: Apr. 9, 2002

(54) MONITORING OF THE PRESSURE OF A PRODUCT FLUID TO BE ADMINISTERED IN DOSED AMOUNTS DURING INFUSION OR INJECTION

(75) Inventors: Urs Kipfer, Lützelflüh; Erich Imhof, Utzenstorf, both of (CH)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 09/391,330

(22) Filed: Sep. 7, 1999

(30) Foreign Application Priority Data

Sep. 8, 1998 (DE) .......................................... 198 40 992

(51) Int. Cl.⁷ ............................................. A61M 31/00
(52) U.S. Cl. ........................ 604/506; 604/67; 604/225; 604/224; 222/309; 222/390
(58) Field of Search ................................ 604/236, 237, 604/67, 65, 500, 506, 224, 225; 222/630, 390, 631, 336, 309, 333, 52, 396

(56) References Cited

U.S. PATENT DOCUMENTS

| | | | |
|---|---|---|---|
| 3,884,228 A | | 5/1975 | Hahn |
| 4,090,640 A | * | 5/1978 | Smith et al. ................... 222/52 |
| 4,298,575 A | * | 11/1981 | Berglund ..................... 222/309 |
| 4,562,751 A | | 1/1986 | Nason et al. .................. 74/111 |
| 4,969,874 A | | 11/1990 | Michel |
| 5,084,060 A | | 1/1992 | Freund et al. |
| 5,188,259 A | * | 2/1993 | Petit ........................... 222/390 |
| 5,209,739 A | | 5/1993 | Talalay |
| 5,336,183 A | | 8/1994 | Greelis et al. |
| 5,453,097 A | | 9/1995 | Paradis |
| 5,743,872 A | | 4/1998 | Kelly |
| 5,788,673 A | | 8/1998 | Young et al. |
| 5,827,244 A | | 10/1998 | Boettger |
| 5,913,455 A | * | 6/1999 | La et al. ...................... 222/309 |
| 5,934,510 A | * | 8/1999 | Anderson .................... 604/237 |
| 6,131,766 A | * | 10/2000 | King et al. ................... 222/390 |

FOREIGN PATENT DOCUMENTS

| | | |
|---|---|---|
| AU | 5861273 | 1/1975 |
| DE | 2819900 | 11/1978 |
| DE | 3922291 | 11/1990 |
| DE | 19717107 | 11/1998 |
| EP | 0143895 | 6/1985 |
| WO | WO 9415660 | 7/1994 |
| WO | WO 9627398 | 9/1996 |
| WO | WO 9700091 | 1/1997 |

* cited by examiner

Primary Examiner—Angela D. Sykes
Assistant Examiner—Jeremy Thisse
(74) Attorney, Agent, or Firm—Dorsey & Whitney LLP

(57) ABSTRACT

The invention relates to a process for the monitoring of the pressure of a product fluid to be administered in dosed amounts during an infusion or injection, which is dispensable from a container that is received in or formed by a housing, by advancement of a piston received in the container. The reaction force exerted by the piston onto the housing, which serves as a measure for the fluid pressure, is hereby measured and fed to a control for a drive of the piston. The control compares the measured reaction force with a predetermined reference force and controls the drive of the motor under consideration of the result of the comparison. The reference force is a nominal value for the reaction force and a direct nominal/actual comparison is carried out between the measured reaction force and its nominal value. The invention further relates to an apparatus which is especially suited for carrying out the process.

32 Claims, 4 Drawing Sheets

MONITORING OF THE PRESSURE OF A PRODUCT FLUID TO BE ADMINISTERED IN DOSED AMOUNTS DURING INFUSION OR INJECTION

BACKGROUND OF THE INVENTION

1. Technical Field

The invention relates to the monitoring of the pressure of a product fluid to be administered in dosed amounts during infusion or injection.

2. Description of the Related Art

During infusion or injection of a product fluid, the exact dosing of the administered product is of large importance, especially upon dosed administration to humans. If the administration is largely automated, as, for example, in insulin treatment with portable infusion pumps, monitoring of the proper product administration is desired, if not a must. A significant possibility for the monitoring is the monitoring of the product fluid pressure, since during proper functioning of the mechanical and electronic components of an infusion or injection apparatus, a proper product administration can be inferred as long as the fluid pressure remains within a preselected pressure range. Upon noncompliance, an occlusion or leakage in the fluid guide system can be inferred. Leakages and occlusions present a risk, especially during the automated administration of active substance solutions in the medical or veterinary field because of the danger of non-detection or detection too late.

Infusion pumps wherein the pressure of the product fluid to be administered is monitored in order to detect blockages in the fluid guiding system are known, for example, from U.S. Pat. No. 4,562,751, and WO 96/27398. These two references relate to infusion pumps wherein a product fluid is conveyed from a container containing the product by displacement by means of a piston. The piston is linearly displaceable in the container and is driven by a spindle drive positioned parallel to a displacement axis of the piston. A spindle drive element is mounted in the housing of the infusion pump for rotation around its longitudinal axis and supported for displacement in direction of its longitudinal axis. A nut which acts as a driven member and moves on the spindle is secured in the housing against rotation and coupled with the piston in such a way that it moves the piston along during its own linear displacement.

With its free end on one end surface, the spindle according to U.S. Pat. No. 4,562,751 engages a thrust switch which upon exceeding of a threshold pressure stops the pump. This threshold pressure is reached when the piston is not moveable in the container or only with excessively large force. In such a case, the spindle because of its rotation in the nut, moves opposite the displacement direction of the piston and against the thrust switch.

It is mentioned in WO 96/27398 as a disadvantage of such type of pressure monitoring that upon use of such a high pressure limit switch, an occlusion is not indicated in time, since, first, several product dosages, which should have been administered in series, must so to speak accumulate in order to build up the threshold pressure for the switch. The WO 96/27398 suggests the use of a force sensor instead of the use of a high pressure limit switch, which force sensor outputs a signal which is proportional to the measured force and, thus, the fluid pressure in the container. The pressure monitoring consists of detecting the fluid pressure by the force sensor at two different points in time by measuring of the reaction force exerted by the piston during its advance in the container, and comparing the two signals output by the force sensor with one another. Therein a first measurement takes place during administration of the product fluid and a second measurement later before administration of the subsequent product dose. If a preselected difference between the two signals is not reached, an occlusion is indicated and an alarm signal activated. If the difference exceeds the preselected signal difference, this then indicates that the pressure in the container has fallen, and that product fluid is in fact administered in the required manner. This type of pressure monitoring takes substantial time. Furthermore, only occlusions are detectable.

SUMMARY OF THE INVENTION

It is an object of the invention to enable a pressure monitoring of a product fluid to be administered in dosed amounts during infusion or injection wherein malfunctions are detected as quickly and reliably as possible.

The invention is based on a monitoring of the pressure of a product fluid to be administered in dosed amounts during infusion or injection wherein the product fluid is dispensable or dispensed from a container by advancing a piston received in the container. The product fluid is understood to be especially a liquid solution of an active substance. The container is received in a housing or formed by the housing itself. As measure of the fluid pressure, a reaction force is measured which is exerted by the piston during advancement and is fed to a control for a drive of the piston. The control compares this measured reaction force with a preselected reference force and controls the drive of the piston in accordance with the comparative results resulting therefrom.

In accordance with the invention, the reference force is a nominal value for the reaction force and a direct nominal/actual comparison is carried out between the measured reaction force and its nominal value. This at least one nominal value is stored and can always be recalled by the control for the purpose of the nominal/actual comparison for comparing it with the actual reaction force measured during a dispensing operation, especially an administration or priming. The reaction time in case of a malfunction determined during the monitoring can be held as short as possible by the control making the direct comparison between the actually measured reaction force and its nominal value, i.e., measuring the difference between nominal and actual.

Preferably, the control only monitors or controls the actual reaction force and only in the case where a preselected maximum admissible difference between nominal and actual is exceeded reacts with the shutdown of the drive and appropriately also with the activation of an alarm. Apart from this consideration in accordance with the invention, the control as part of the drive control can also start a program as is done by conventional controls.

In an especially preferred embodiment, a valve is positioned in the path of the product fluid between the outlet of the container and the exit location, for example, the forward end of an infusion needle, said valve causing a predefined pressure drop. The pressure drop is preferably selected so that a leaking of product fluid from the container because of gravity is safely prevented during all conditions occurring during the practical use of the device. For the construction and positioning of such a valve, reference is made to German Patent Application No. 197 23 648, the disclosure of which is herewith incorporated. The valve is preferably positioned as closely as possible to the exit location of the product fluid in order to include the whole fluid conducting system into the leakage monitoring. If the valve is positioned in the flow path of the product fluid immediately after the container outlet, which corresponds to another preferred embodiment, leakage between the piston and the valve can still be detected.

Additionally acting forces can be neglected compared to the valve action. That reaction force which results based on the nominal value for the pressure drop of valves of a valve model series is used as the nominal value. The control is adjusted to this nominal value by the manufacturer. The permissible range for the actual reaction force is preselected such that it corresponds to that range of the reaction force which results from the spread of the nominal value for the pressure drop of the valves of the model used. The spread range around the nominal value is upwardly and downwardly extended in order to also consider deviations of other components, for example, the drives used. However, the valve deviation is here also foremost the determining factor. To build the corresponding threshold values regarding an occlusion and a leakage, the deviation ranges can be increased by tolerance margins. An occlusion is then assumed when the measured reaction force falls upwardly outside the nominal value range predetermined in this way. A leak is assumed if it falls downwardly outside the so-predetermined nominal value range. The valve with defined pressure drop is an advantage, especially for the leak monitoring.

If such a valve is not present or if the pressure drop created by the valve is only so large that the additionally acting forces cannot be neglected in good approximation, several nominal values to be considered for a dispensing operation with the associate upper and lower limits can be preselected. A first nominal value can then be predetermined for that force which must be exerted in order to move the piston in the container forward from a rest position. This force corresponds essentially to that which must be exerted to overcome the contact friction between the piston and the container wall and the flow resistances. Since the speed of advancement during dispensing of the product fluid is generally constant, the piston in the constant phase of its advancement exerts a constant reaction force on its support, the housing, when the catheter is filled. A second nominal value then corresponds essentially to the force which is necessary for overcoming the piston slide friction and the flow resistances which the product fluid encounters on its path from the container to the exit location. Such flow resistances represent, for example, a narrowed outlet of the container, the catheter connected thereto, and an infusion needle connected to a free end of the catheter. An occlusion is preferably then assumed when the measured reaction force exceeds the first nominal value by a preselected maximum amount. A leak is preferably then assumed when the measured reaction force during advancement of the piston is smaller than the second nominal value by a preselected amount.

Nominal values can also be selected in the form of a course of the nominal value over time or the advancement distance which the piston travels during one administration between its position directly before the administration and its position immediately at the end of the administration. The at least one nominal value is in this case a value of a complete nominal value profile or course. Other nominal values of the profile can also be used for comparison purposes.

A priming of the piston or the device can be manually completed or fully automatically carried out. During priming, the piston is advanced from an initial installation position in the container until product fluid exits at the exit location. All fluid conducting parts, essentially the container, the connected catheter and the infusion needle are thereby filled with product fluid after the priming and the first dosed administration can then take place. The completion of the priming can be detected as part of the pressure monitoring in accordance with the invention in that the measured reaction force is monitored if it corresponds or not with the above-mentioned second nominal value after exit of product fluid. When the valve is positioned between the outlet of the container and the needle, this nominal value in good approximation also corresponds to the reaction force generated by the pressure drop between valve inlet and valve outlet.

By comparing the measured reaction force with the at least one nominal value, the fill condition of the container can also be automatically determined. The nominal position of the piston along the axis of displacement of the piston is originally available to the control, since it controls the exact position of the piston drive, preferably a linear drive, relative to a platform. A first contact of the piston drive with the piston can be determined by comparison of the measured reaction force with the at least one nominal value, especially with use of the valve.

In another preferred embodiment, the piston drive is preadjusted by the control in such a way that it stops itself upon first contact against the piston. In this case, the piston position and therefore the fill condition can be determined in an especially simple manner from the known position of the drive motor upon stopping. The use of a self-stopping motor, especially a step motor with a preset or predetermined or adjustable start stop frequency, is principally possible for determination of the fill condition and generally advantageous, i.e., even without the further features of the invention described in connection with the force comparison. The start stop frequency is a maximum frequency, in case of a step motor the maximum pulse frequency, with which the motor starts at a given signal. For a given motor, it is dependent on the momentum to be generated by the motor and is therefore generally presented as a momentum-dependent characteristic frequency line.

A monitoring of the pressure during priming is preferably used for derivation of at least one nominal value for the reaction force, which is specific for each device. The reaction forces during priming itself are compared with the at least one nominal value which is already preset by the manufacturer and, preferably, stored in a non-erasable permanent memory for access by the control.

A reaction force measured during priming is used as an individual nominal value instead of the manufacturer preset nominal value for the pressure monitoring during administration, if the reaction force measured during priming lies within the permissible nominal value range. In that embodiment, the control is adaptive. The sensibility of the pressure monitoring is increased with the adaptive control.

The pressure monitoring in accordance with the invention is most preferably used in portable infusion pump apparatus, as used especially in insulin treatment. In this type of infusion apparatus, the administration of the product fluid, for example, insulin, is almost continuous, in that in short time intervals and over a longer time frame smaller, exactly dosed product doses are administered in the form of many individual administrations. Completely continuous infusions are encompassed by the term administration as are individual injections.

BRIEF DESCRIPTION OF THE DRAWINGS

A preferred embodiment of the invention will be described in the following by way of figures. It shows.

DETAILED DESCRIPTION OF THE PREFERRED EMBODIMENT

Figure 1:
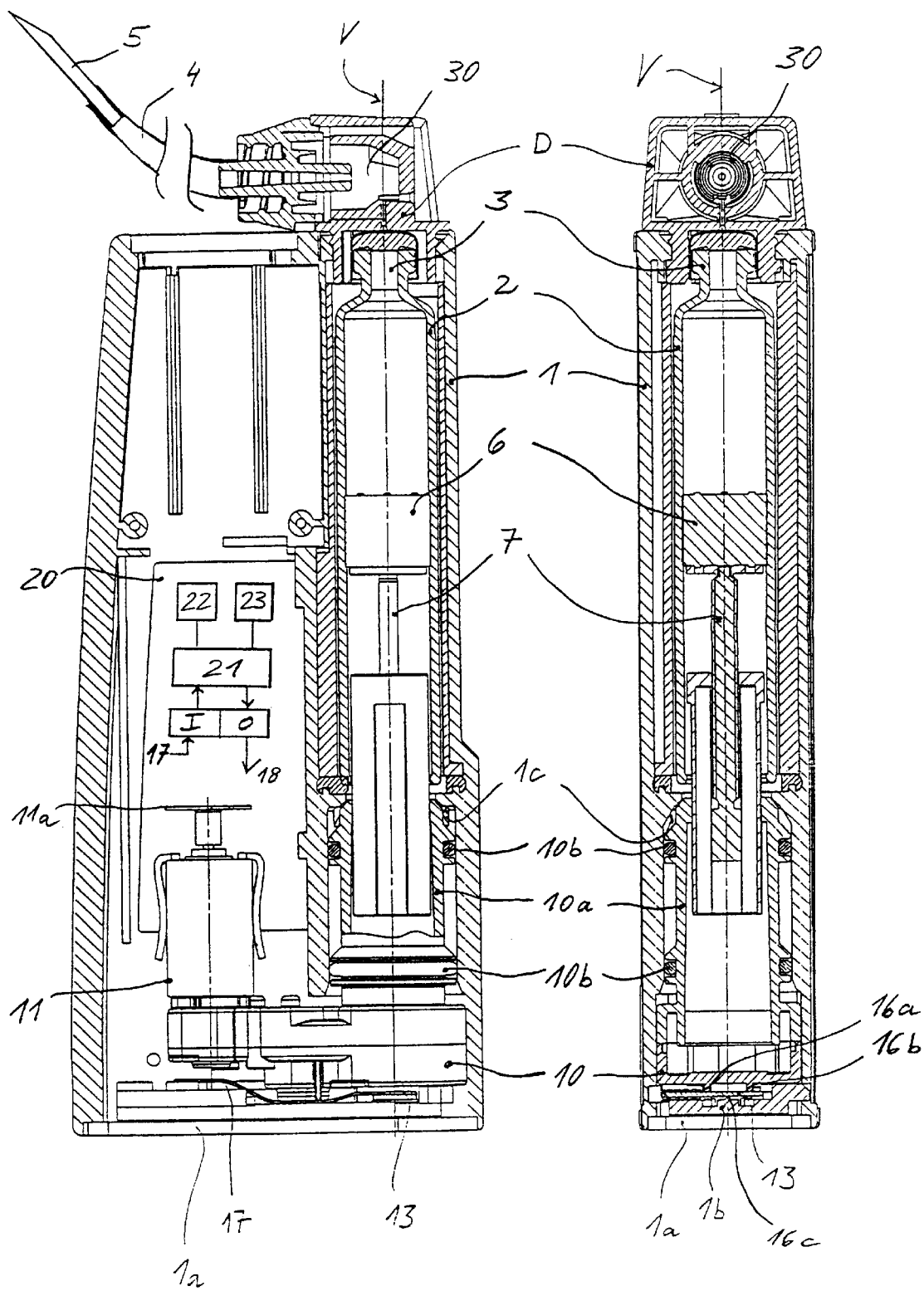
FIG. 1 a longitudinal section through an infusion pump with pressure monitoring.

FIG. 1 shows a portable infusion pump for insulin treatment. The pump, especially its drive, is described in the German Patent Application No. 197 17 107. The disclosure of this application is complementarily referred to.

A container in the shape of an ampulla 2 is received in a pump housing 1. The ampulla 2 is filled with insulin. A piston 6 is received in the ampulla 2 for linear movement in a forward movement direction towards an ampulla outlet 3. The advancement of the piston 6 is achieved by pushing of a driven member 7 constructed as a threaded rod, on a rearward surface of the piston 6. The driven member 7 is part of a spindle drive which is telescopically constructed with two stages. However, the invention is not limited thereto regarding the piston drive.

During advancement of the piston 6 along an axis of displacement V, insulin is dispensed through a catheter connected to the outlet 3 and an infusion needle 5 fastened to the forward, free end of the catheter 4. In order to adjust a defined base pressure in the ampulla 2, a valve 30 is positioned in the flow path of the insulin. Such a valve can be used not only for the definition of a constantly existing base pressure in the fluid conducting system 2 to 5, but also for the prevention of spontaneous draining of the ampulla 2 under the inherent weight of the liquid column in the fluid conducting system 2 to 5. The valve 30 is preferably dimensioned such that it safely prevents such an undesired spontaneous draining under the conditions occurring during the practical use of the infusion pump. In this embodiment, the valve 30 is received in a removable housing cover D with which an ampulla shaft is closed after insertion of the ampulla 2.

The drive of the driven member 7 is carried out by way of a rotary motor 11 through a step down transmission on the spindle drive with the driven member. Reference is made to the German Patent Application No. 197 17 107 with regard to the spindle drive and the step down transmission. At least the threaded rod 7 is guided straight in the housing 1 and secured against rotation so that a rotational driving of two front-mounted drive members of the spindle drive which surround the driven member 7 in the form of a sleeve cause an advancement of the threaded rod 7.

The spindle drive together with the transmission and the motor 11 is mounted on a moveable platform 10, which itself as a whole is secured against rotation in the housing 1 and linearly moveably mounted in and opposite the advancement direction of the piston. Principally, it would also be possible to rigidly mount the motor in the housing as it would also be possible to rigidly mount the motor 11 in the housing together with the transmission. In that case, a corresponding shift engagement would be required between the housing mounted drive component and the input stage then mounted on the moveable platform 10, for example, an interlocking spur gear extending over a corresponding length in direction of advancement.

In order to be able to detect possible malfunctions in the fluid conducting system 2, 3, 4, 5 the pressure of the product fluid, especially the fluid pressure in the ampulla 2, is monitored. A reaction force exerted by the piston 6 onto the housing 1 is measured by way of a force sensor 13 for monitoring of the pressure and compared with a preset nominal value for the reaction force.

That force is measured as reaction force by way of a force sensor 13 which force is exerted from the piston 6 through the threaded rod 7 and the spindle drive on the moveable platform 10 and, because of the movability thereof, onto the force sensor 13. To this end, the moveable platform 10 is floatingly supported on the housing walls in housing 1.

The moveable platform 10 is therefor longitudinally moveably supported with a platform sleeve 10a in a housing sleeve part surrounding this sleeve 10a, by way of elastic supporting elements 10b in the form of a pair of O-rings, for example, rubber rings. The platform sleeve 10a surrounds drive members of the spindle drive which are constructed as drive sleeves. A contact between the moveable platform and the housing 1 is only created through these O-rings 10b. A displacement movement along the displacement axis V takes place between the moveable platform 10 and the housing 1 only upon elastic deformation of the O-rings 10b. The O-rings 10b themselves are displaced neither relative to the housing 1 nor relative to the moveable platform 10, but are only elastically deformed. The frictional forces are minimized by this form of the floating support and the force exerted during the displacement of the piston 6 is largely genuinely transferred to the force sensor 13. The O-rings 10b are received in circumferential grooves of the platform sleeve 10a and in this manner fixed relative to the two opposite surfaces of the housing and the platform sleeve 10a by form fit and force fit. However, they can also be connected with one of these two surfaces by material connection and with corresponding installation, they could also be compressed between the two mutually moveable surfaces and thereby only frictionally held. It should, however, be guaranteed that, with the exception of the elastic deformation forces, no further friction forces should act upon displacement of the moveable platform 10.

The force sensor 13 is positioned between a rearward end surface of the moveable platform 10 and a wall of the housing 10 opposite this rearward end surface. It is further positioned in the extension of the axis of displacement V of the piston 6 so that the reaction force acting along the axis of displacement V of the piston 6 acts directly on the force sensor 13. The reaction force is exerted symmetrically to the axis of displacement V. A tilt momentum by the reaction force can thereby not be generated.

Figure 2:
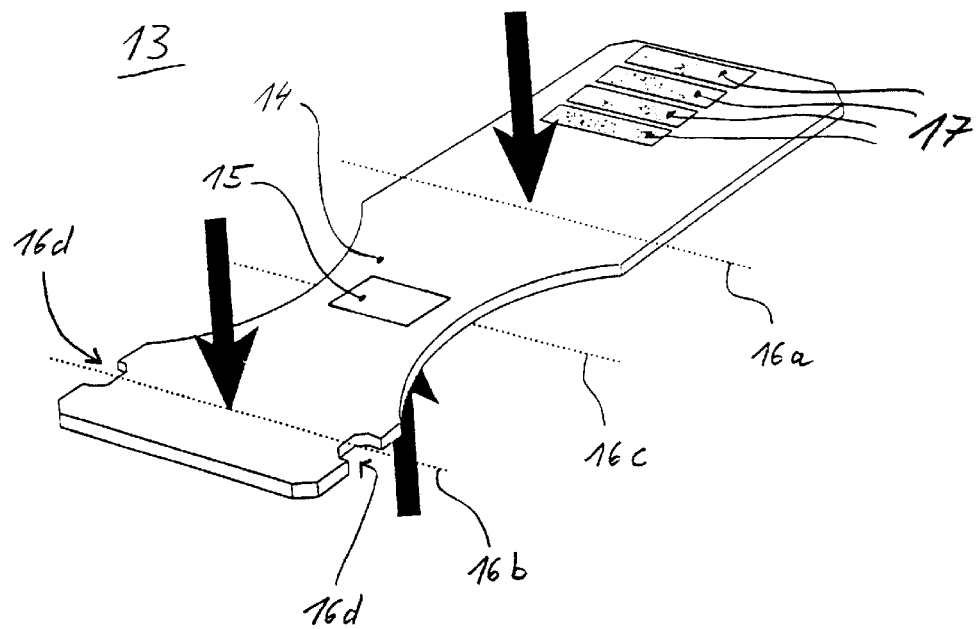
FIG. 2 a pressure sensor for the pump according to FIG. 1.
Figure 2:
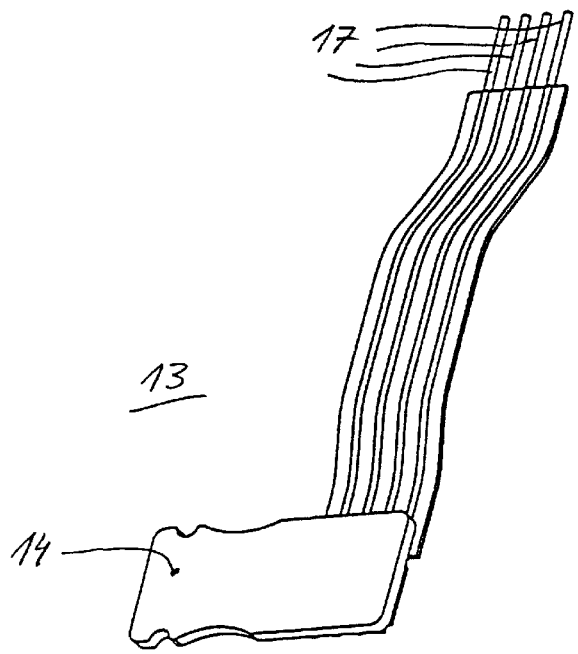

The force sensor 13 is separately illustrated in FIG. 2. It is formed by a bendable beam 14 on which a thin film extension measurement strip 15 is placed at least on one beam surface. A measured value amplification could be achieved by placement on both opposite beam surfaces. Four conductors of a bridge circuit are designated by 17. In this form of the bendable beam, two spaced apart parallel webs 16a and 16b (FIG. 1) on the one beam surface are illustrated as platform side, linear supports, between which the beam 14 with the extension measurement strip 15 is bent by the reaction force exerted by the piston 6. For the exact definition of the location of application of the reaction force, a further web 16c extends from the ground plate 1b from the under side of the housing opposite the two webs 16a and 16b, and exactly in the middle between these two webs 16a and 16b (FIG. 1), the linear contact of which is indicated in FIG. 2. The linear contact of the third web 16c is located in the extension of the axis of displacement V and parallel to the webs 16a and 16b. The three webs 16a, 16b and 16c are of rounded cross section in the region of contact so that the reaction force along the web 16a and 16b is introduced linearly as exactly as possible and the bearing force also linearly acts on the web 16c of the bendable beam 14. Other cross sectional shapes which cause this or approximate it are also suitable. Other sensors, for example, piezo-resistive sensors would also be useable instead of the extension measurement strip within the framework of a static measurement process.

Figure 3:
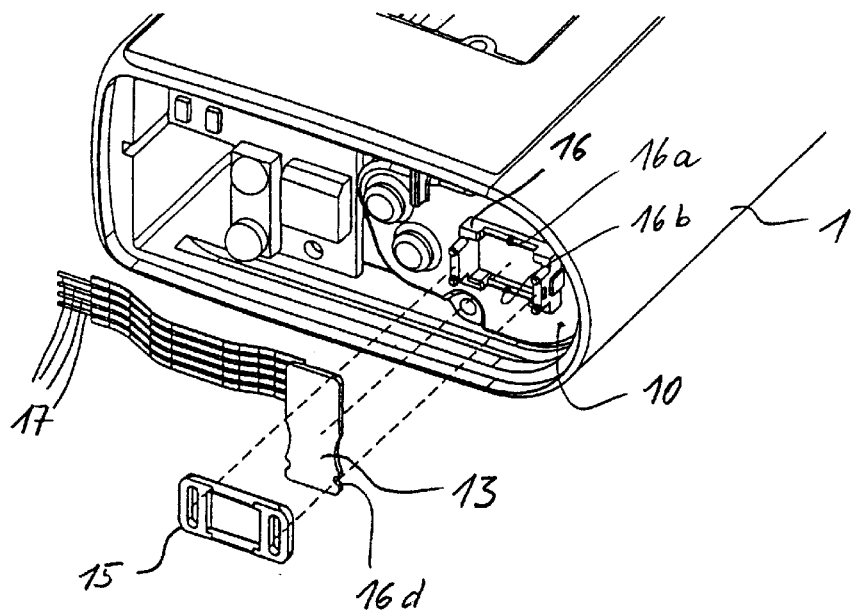
FIG. 3 a moveable platform of the pump according to FIG. 1 with a pressure sensor.
Figure 3:
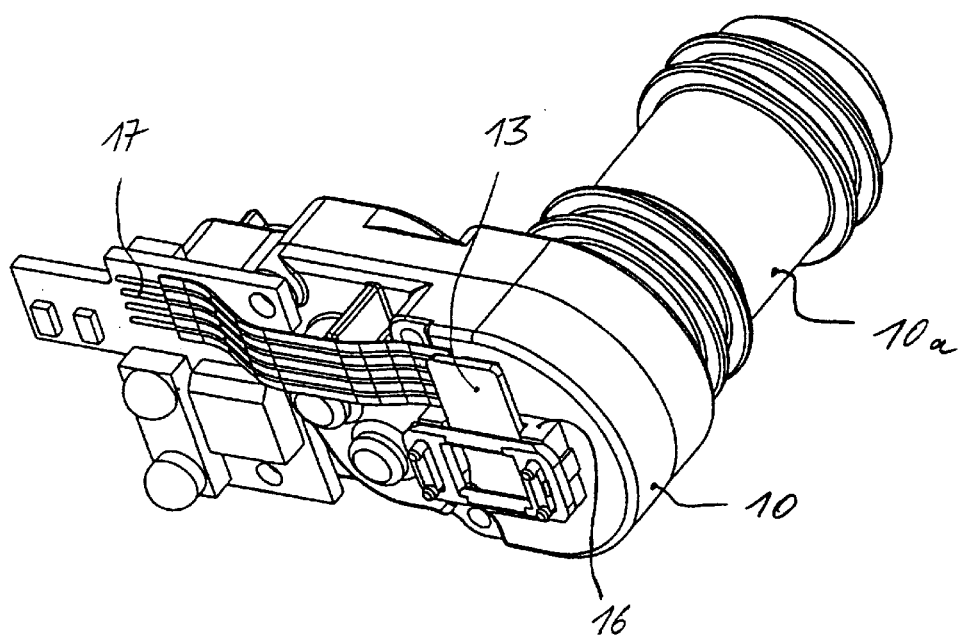

The positioning of the force sensor 13 on the moveable platform is best apparent from the view in combination of the two drawings of FIG. 3. The upper drawing thereby shows the moveable platform 10 in its installed location in the housing 1, while the lower drawing shows the moveable platform 10 as a separate installation module. A positioning and fastening arrangement 16 for the force sensor 13 is positioned on the underside of the moveable platform 10. This arrangement 16 forms at the same time the parallel webs 16a and 16b and a guide arrangement for the force sensor 13 as well as a small fastening plate 15. The force sensor 13 is provided with two lateral notches 16d for the purpose of its exact positioning relative to the webs 16a and 16b, which notches cooperate with the guide arrangement of the positioning and fastening arrangement 16. In this embodiment, a guide pin projecting from the positioning and fastening arrangement 16 is respectively located in each of the two notches 16d.

The positioning of the drive 7 to 11 on the common moveable platform 10 has also manufacturing advantages. Namely, the drive can hereby completely preassembled on or integrated with the moveable platform 10. The moveable platform 10 is subsequently inserted into the housing as a whole through a rearwardly open end surface of the housing 1. The required contacts to the power supply and control of the motor 11 are also made during assembly. In this embodiment, wherein the motor is also moveable together with the moveable platform 10, the contacts are formed by plug-in contacts at both ends of a connecting conduit and the movements taken up by the flexible connecting conduit. The contacts for the motor 11 can also be formed as slide contacts. After insertion of the moveable platform 10, a base plate 1b is inserted into the rearwardly open housing end surface and fixed to the housing 1. The third web 16c is formed on the base plate 1b. Finally, the housing 1 is closed by way of a cover 1a. The moveable platform 10 is now free floatingly supported only by the O-rings 10b relative to the housing 1 and between the third web 16c on one side and a shoulder 1c which on the housing side is opposite the moveable platform 10 as seen in direction of displacement of the piston 6.

In this initial installation position of the moveable platform 10, no contact exists between the threaded rod 7 and the piston 6. As long as a contact does not take place, i.e., in its initial installation position, the moveable platform 10 has a small amount of looseness between the housing side shoulder 1c and the force sensor 13.

A measured value representing the impressed reaction force, preferably a measured value proportional to the reaction force, preferably in the form of an electrical signal, is distributed from the force sensor 13 through a conduit 17 to a control 20 for the motor 11. The measured value which represents the actually measured reaction force is permanently present at an input I of the control 20. The control 20 is connected with the motor 11 through an output O and a corresponding control conduit or a control bus 18. The motor 11 is position-controlled.

The motor 11 is a step motor with a physically predetermined start-stop-frequency. This is a frequency and corresponding motor speed upon the exceeding of which the motor torque decreases, whereby the motor is arrested, if it encounters a relatively small resistance in this condition. After arresting, it no longer starts up by itself, but only swivels back and forth until it is completely stopped. It is subsequently once again started by a control command of the control 20.

The position of the motor 11 is monitored by way of a propeller wheel 11a and an optical sensor cooperating therewith for which the propeller wheel 11a functions as light beam interrupter. The control 20 stops the motor 11 if a control impulse does not lead to motor rotation. The motor position is available to the control 20 at least in form of the number of rotations made at any point in time from a reference position. The motor position can possibly also be determined by way of a counter connected to the optical sensor which counts the number of interruptions by the blades of the propeller wheel. The position of the threaded rod relatively to the moveable platform 10 is also available to the control and, finally, also the position of the piston 6 in the ampulla 2.

The control 20 includes a microprocessor 21 with two permanent memories 22 and 23. A standard nominal value course S for the reaction force is stored in memory 22. The further memory 23 is written to during priming of the infusion pump. The control 20 is connected with the motor 11, the force sensor 13 and further components, especially a power source, by way of an interface I/O. The connection to the force sensor 13 is indicated by the reference number 17 and the one to the motor with the reference number 18.

During priming, the threaded rod 7 is driven onto the piston 6 from a starting condition wherein the ampulla 2 is inserted into the housing 1 and its closure membrane at the outlet 3 is penetrated by a connecting needle. Until the contact with the piston 6, the motor 11 runs at fast speed significantly above the start-stop-frequency. At the fast speed, it is operated at a pulse frequency which is preferably at least twice as large as the start-stop-frequency. As soon as the threaded rod contacts the piston 6 with its plunger, the motor automatically stops, since its torque above the start-stop-frequency is not sufficient to drive the threaded rod 7 and the piston 6. The stop position of the motor 11 is registered in the control 20 and stored as base position for the product dispensing. If for the used ampulla type a suited reference value is stored in the control 20 for a specific piston position, the control 20 can determine from a comparison of this reference value with the actual piston position determined during driving against the piston if the ampulla is a full or, for example, half full ampulla.

Although preferred, a step motor with adjustable and accordingly preadjusted start-stop-frequency need not be used. The piston position in the ampulla 2 can also be determined by way of the force sensor 13, since during the driving against the piston 6, a reaction force builds up because of the floating support of the moveable platform 10 which, in the end, pushes the moveable platform 10 with the force sensor 13 against the web 16c. The thereby bent force sensor 13 gives off a measured value for the reaction force taken up. By way of this measured value, the control 20 can also determine if the threaded rod 7 has contacted the piston 6, and in which position at this point in time the piston 6 is found in the ampulla.

In this embodiment, the motor 11 which is a step motor with adjustable start-stop-frequency is automatically started again after the above-described stopping so that now the piston 6 is advanced in the ampulla 2. As part of the priming, the piston 6 is pushed in the ampulla 2 towards the outlet 3 until insulin exits at the exit location of the infusion needle 5. As soon as fluid emergence is safely determined, the threaded rod and, thereby, the piston 6 are stopped in the displacement position reached at that point in time along the common axis of displacement V. The stopping can be carried out manually when the emergence is observed by the user, or automatically by the control 20.

By way of the pressure monitoring in accordance with the invention, it is possible to use the priming itself for the production of one or more nominal values or a nominal value course for the reaction force, whereby the nominal values produced during the priming are specific for the respective injection or infusion device. In order to enable the individualization of the pressure monitoring, the memory 23 is programmable, preferably it is a so-called EPROM or Flash-ROM. The memory 22 for the storage of standard nominal values is formed as a read-only memory. Principally, both memories 22 and 23 can of course also be formed as a single programmable memory, whereby the standard nominal value (S) would be assigned to their own memory region and this memory region would be exempt from possible erase procedures.

Figure 4:
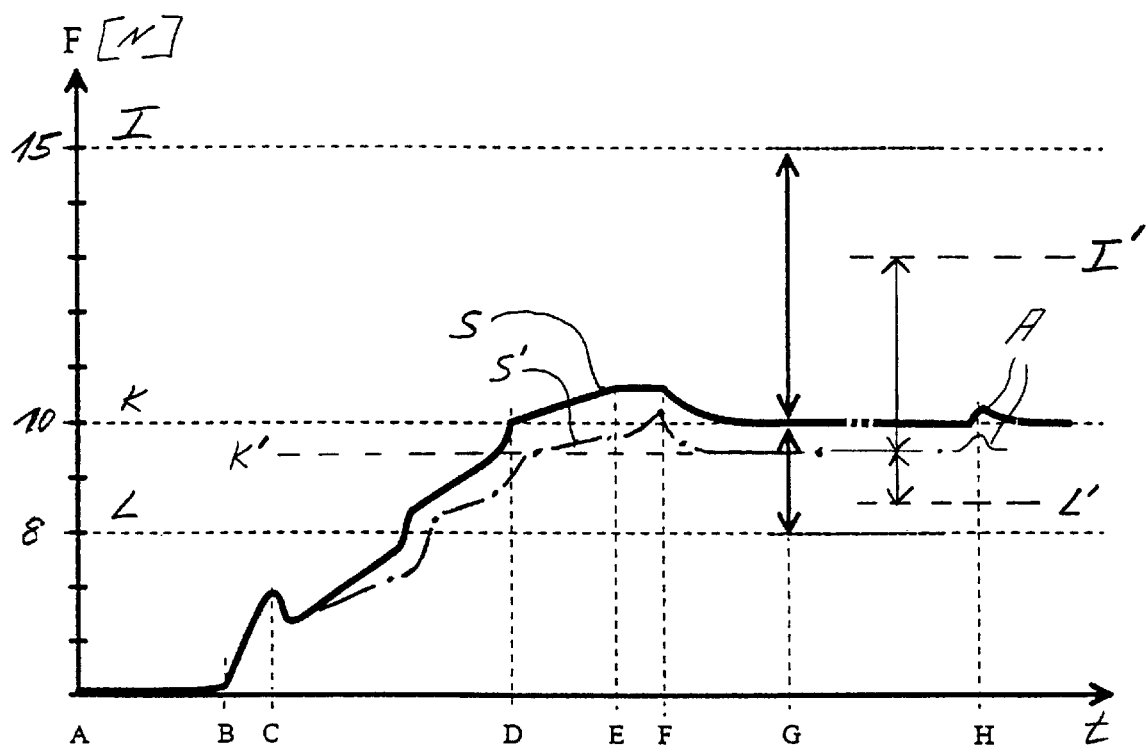
FIG. 4 a standard nominal value course and an individual nominal value course, as determined during priming.

FIG. 4 shows a time-force-diagram of a standard nominal value course S plotted over time T, as stored in memory 22. In addition to the standard nominal value course S entered as a continuous line, a nominal value course S' is entered as a broken line which has occurred during priming and occurs thereafter still. In the time T, calculated from a point in time A which represents the first switching on of the device after an ampulla exchange, the piston upon execution of the stored program exerts the reaction force S'. The standard nominal value course S is the same for all devices of one model. At least one nominal value therefrom significant for the monitoring is preset by the device manufacturer, i.e., the infusion pump, is delivered preadjusted in this way. The standard nominal value course S can be empirically determined by the manufacturer or through simulation, and stored in the memory 22.

The standard nominal value course S includes the priming and is also used for the monitoring thereof. During priming, the reaction force course which is specific for the respective pump and which thereafter serves as individual nominal value course S', is run through which continues over the later dispensing operations A. The priming process is started from the installation position, the reference position at the point in time A. For the priming, the threaded rod 7 is initially driven from the installation position against the piston 6 in the position at the point in time B. The distance between the points in time A and B is covered by the motor 11 at high speed with, for example, 1200 steps or pulses per second (pps=pulses per second). The position at the point in time B is determined and stored. For the whole remainder of the program, the motor is then driven with, for example, 200 pps. Once the reaction force has exceeded the force required for overcoming the contact friction, which is the case at C, the piston 6 starts to move in the ampulla 2. The reaction force subsequently further increases until the valve 30 is filled with product fluid, which is the case in the position at the point in time D. The reaction force or its nominal value S required for overcoming the valve counter pressure PV is referred to as K, the value measured during priming as K'. Thereafter, the catheter fills downstream of the valve 30. Immediately before the first fluid expulsion at the needle, a maximum value is reached in the position at the point in time E. The motor is stopped by the user at F, after fluid expulsion has been observed. After fluid expulsion has taken place and, especially after stopping of the device by the user, the reaction force sinks once again to K'. After determining the fluid expulsion either by observation or automatically by determining the decrease at G, the measured force K' is stored as individual nominal value of the infusion pump, and used instead of the standard nominal value K for the later administration, if the relationship L<K'<I is complied with. I and L are the limits of the measured reaction force allowed for the infusion pumps of one model, and are derived from the standard nominal value K typical for the device model. L is about 20% under and I about 50% above K. I is an occlusion threshold value and L is a leakage threshold value. The then occurring peaks represent the reaction force values for the individual bolus doses at the points in time H of the product administration.

The standard nominal value K corresponding to the pressure drop at the valve with permissible maximum deviations I–K and K–L or directly in form of the range limit I and L principally suffices as single set nominal value. The monitoring can be more exactly adapted to the actual conditions and refined by optimal adaptation of this set nominal value to the individual nominal value K'. The permissible maximum deviations I'–K' and K'–L' from K' can be smaller than those from K, since device related tolerances are already compensated by the transition to the individual nominal value K'.

The priming can also be fully automated by a comparison with the standard nominal value course S or even only with the nominal value K. The successful completion of the priming and also the fill condition of the ampulla 2 determined thereby can be displayed for the user on a display of the infusion pump. Upon identification of possible occlusions, preferably also of leakages, the motor 11 is stopped by the control 20 through the conduit 18. Such malfunctions can be brought to the attention of the user by corresponding display means and alarm means.

The pressure monitoring in accordance with the invention by way of direct force measurement and immediate comparison of the measured value output by the force sensor 13, which represents the fluid pressure present in the ampulla 2, with a nominal value allows an extremely quick identification of an inadmissible pressure condition. The invention further makes possible a significant fine tuning of the monitoring in that, so to speak, by way of an intermediate step, an individual nominal value or nominal value course is produced for comparison during the actual administration. The reliability of the pressure monitoring is thereby significantly increased. Finally, the pressure monitoring, in accordance with the invention, is advantageously useable in many respects in that not only occlusions, but also leakages can be identified and, beyond that, the priming can be automated and even the fill condition of the ampulla can be automatically determined.

In the foregoing description a preferred embodiment of the invention has been presented for the purpose of illustration and description. It is not intended to be exhaustive or to limit the invention to the precise form disclosed. Obvious modifications or variations are possible in light of the above teachings. The embodiment is chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. Process for the monitoring of the pressure of a product fluid to be administered in dosed amounts during an infusion or injection, said product fluid being dispensable from a container (2), which is received in a housing (1) or formed by the latter, through advancement of a piston (6) received in the container (2), wherein
   a) a reaction force exerted by the piston (6) onto the housing (1), which serves as a measure for the pressure, is measured and fed to a control (20) for a drive (7 to 11) of the piston (6) and
   b) the control (20) compares the measured reaction force with a predetermined reference force and controls the drive (7 to 11) of the piston (6) under consideration of the result of the comparison, characterized in that
   c) the reference force is a nominal value (S; S') for the reaction force and a direct nominal/actual comparison is carried out between the measured reaction force and its nominal value (S; S').

2. Process according to claim 1, characterized in that the nominal value (S') relied upon for the comparison with the measured reaction force is determined by measuring during a priming of the piston (6), in which the piston (6) is displaced from an installation position in the container (2) up to an expulsion of product fluid in a starting position for a first administration.

3. Process according to claim 2, characterized in that the reaction force measured during priming is compared with a predetermined standard nominal value (S) and upon compliance with a predetermined, maximum permissible difference to the standard nominal value (S) is used as new nominal value (S') during the administration.

4. Process according to claim 1, characterized in that a defined pressure drop (PV) is produced in a flow cross section of the product fluid between the container (2) and an infusion or injection needle (5).

5. Process according to claim 1, characterized in that during a priming of the piston (6), in which the piston (6) is advanced from an installation position in the container (2) until an expulsion of product fluid in a starting position for a first administration, a first striking of the drive (7 to 11) against the piston (6) is detected and the fill condition of the container (2) is determined from the position of the drive (7 to 11) upon contact.

6. Process according to claim 1, characterized in that a start-stop-frequency of a step motor (11) of the drive (7 to 11) is adjusted such that the step motor (11) is arrested upon a first contact of the drive (7 to 11) on the piston (6) and that a fill condition of the container (2) is determined from a position of the motor (11) held upon striking.

7. Process according to claim 1, characterized in that at least a first nominal value and a second nominal value for the reaction force are predetermined wherein the first nominal value represents a reaction force to be exerted for a displacement of the piston (6) from an at rest position and the second nominal value represents a reaction force which adopts a constant value during the displacement movement of the piston (6).

8. Apparatus for the monitoring of the pressure of a product fluid which is dispensable in dosed amounts for the purpose of an infusion or injection from a container (2) by advancement of a piston (6) received in the container (2), wherein the apparatus comprises:
   a) a housing (1) receiving the container (2) or forming the latter,
   b) a force sensor (13) which measures a reaction force serving as a measure of the pressure and exerted by the piston (6) onto the housing (1) and outputs it as a measured value, and
   c) a control (20) which compares the measured value with a predetermined reference value and controls a drive (7 to 11) for the piston (6) under consideration of the result of the comparison, characterized in that,
   d) at least one nominal value (S; S') for the reaction force is stored in a memory (22, 23) of the control (20) and used for a direct nominal/actual comparison with the measured reaction force.

9. Apparatus according to claim 8, characterized in that a standard nominal value (S) for the reaction force is stored in a first memory (22) of the control (20), the reaction force is measured by the force sensor (13) during a priming of the piston (6), compared with the standard nominal value (S) and upon compliance with a predetermined, maximum permissible difference between the standard nominal value (S) and this reaction force stored in a second memory (23) of the control (20) and is used as for the apparatus specific nominal value (S') for the nominal/actual comparison during infusion or injection.

10. Apparatus according to claim 8, characterized in that the force sensor (13) is positioned in alignment with an axis of displacement (V) of the piston (6).

11. Apparatus according to claim 8, characterized in that a driven member (7) directly acting on the piston (6) and a drive member of the drive (7 to 11) directly coupled with the driven member (7) are floatingly and linearly displaceable supported in the housing (1).

12. The apparatus of claim 11, wherein a motor is used for the driving of the drive member.

13. Apparatus according to claim 8, characterized in that the force sensor (13) includes a bendable beam (14), the bending of which, caused by the reaction force exerted thereon, acts on a strain gauge (15) which outputs a measured value corresponding to its stretching or compression.

14. Apparatus according to claim 8, characterized in that a valve (30) is positioned in a flow cross section of the product fluid between the container (2) and an infusion or injection needle (5), said valve (30) permitting flow of the product fluid in direction of the needle (5) only upon exceeding of an over pressure defined by the valve (30).

15. A process for monitoring the pressure of a product fluid to be administered during an infusion or injection, the product fluid being dispensable from a container which is received in a housing or formed by the latter through advancement of a piston received in the container, comprising the steps of:
   a) measuring a reaction force exerted by the piston on the housing and feeding the measurement to a control for a drive of the piston; and
   b) comparing the measured reaction force with a predetermined reference force and controlling the drive of the piston as a result of the comparison, wherein the reference force is a nominal value for the reaction.

16. The process of claim 15, wherein the nominal value relied upon for the comparison with the measured reaction force is determined by measuring during a priming of the piston, in which the piston is displaced from an installation position in the container up to an expulsion of product fluid in a starting position for a first administration.

17. The process of claim 16, wherein the reaction force measured during priming is compared with a predetermined standard nominal value and upon compliance with a predetermined, maximum permissible difference to the standard nominal value is used as new nominal value during the administration of the fluid.

18. The process of claim 15, wherein a defined pressure drop is produced in a flow cross section of the product fluid between the container and an infusion or injection needle.

19. The process of claim 15, wherein during a priming of the piston, the piston is advanced from an installation position in the container to a starting position for a first administration, wherein a first striking of the drive against the piston is detected and the fill condition of the container is determined from the position of the drive upon contact.

20. The process of claim 15, wherein a start-stop-frequency of a step motor of the drive is adjusted such that the step motor is arrested upon a first contact of the drive on the piston, and that a fill condition of the container is determined from a position of the motor held upon striking.

21. The process of claim 15, wherein at least a first nominal value and a second nominal value for the reaction force are predetermined, wherein the first nominal value represents a reaction force to be exerted for a displacement of the piston from an at rest position and the second nominal value represents a reaction force which adopts a constant value during the displacement movement of the piston.

22. An apparatus for monitoring the pressure of a product fluid which is dispensable in dosed amounts for the purpose of an infusion or injection from a container by advancement of a piston received in the container, comprising:
   a) a housing;
   b) a force sensor which measures a reaction force which serves as a measure of the pressure exerted by the piston and outputs it as a measured value; and
   c) a controller which compares the measured value with a predetermined reference value and controls a drive for the piston under consideration of the result of the comparison, wherein at least one nominal value for the reaction force is stored in a memory of the controller and used for a direct nominal/actual comparison with the measured reaction force.

23. The apparatus of claim 22, wherein:
   a) a standard nominal value for the reaction force is stored in a first memory of the control;
   b) the reaction force is measured by the force sensor during a priming of the piston;
   c) the reaction force is compared with the standard nominal value; and
   d) upon compliance with a predetermined, maximum permissible difference between the standard nominal value and this reaction force, the reaction force is stored in a second memory of the control and is used for the apparatus specific nominal value for the nominal/actual comparison during infusion or injection.

24. The apparatus of claim 22, wherein the force sensor is positioned in alignment with an axis of displacement of the piston.

25. The apparatus of claim 22, wherein a driven member directly acting on the piston and a drive member of the drive directly coupled with the driven member are floatingly and linearly displaceably supported in the housing.

26. The apparatus of claim 22, wherein the force sensor includes a bendable beam, the bending of which, caused by the reaction force exerted thereon, acts on a strain gauge which outputs a measured value corresponding to its stretching or compression.

27. The apparatus of claim 22, wherein a valve is positioned in a flow cross section of the product fluid between the container and an infusion or injection needle, the valve permitting flow of the product fluid in direction of the needle only upon exceeding of an over pressure defined by the valve.

28. A pressure monitoring system for an injection or infusion device, comprising:
   (a) a force sensor which measures a reaction force of a piston on a drive; and
   (b) a control, the control comprising a microprocessor, and at least one permanent memory, wherein the at least one permanent memory contains a predetermined standard nominal value, and the at least one permanent memory contains the measured reaction force and compares the measured reaction force to the standard nominal value.

29. The pressure monitoring system of claim 28, wherein the force sensor is a bendable beam with a strain gauge.

30. The pressure monitoring system of claim 28, wherein the at least one permanent memory contains permissible deviations from the standard nominal value.

31. The pressure monitoring system of claim 30, wherein a force measurement outside of the deviations indicate a leakage.

32. The pressure monitoring system of claim 30, wherein a force measurement outside of the standard deviation indicates an occlusion.

* * * * *

UNITED STATES PATENT AND TRADEMARK OFFICE
CERTIFICATE OF CORRECTION

PATENT NO. : 6,368,314 B1
DATED : April 9, 2002
INVENTOR(S) : Urs Kipfer

It is certified that error appears in the above-identified patent and that said Letters Patent is hereby corrected as shown below:

Column 11,
Lines 5, 7, 24, 35, 39, 43, 50, 61, 62 and 64, please delete "(2)".
Lines 5, 9 and 64, please delete "(1)".
Lines 6, 8, 11, 14, 42, 49, 55, 58 and 62, please delete "(6)".
Lines 10 and 12, please delete "(20)".
Lines 10-11, 14, 41, 43-44, 46-47 and 48, please delete "(7 to 11)".
Lines 16 and 19, please delete "(S;S')".
Lines 21 and 32, please delete "(S')".
Lines 23 and 38, please delete the first and second instance of "(6)".
Lines 29 and 31, please delete "(S)".
Line 34, please delete "(PV)".
Line 36, please delete "(5)".
Lines 46, 47 and 51, please delete "(11)".
Line 66, please delete "(13)".

Column 12,
Lines 1, 5, 15, 24 and 26, please delete "(6)".
Lines 1 and 29, please delete "(1)".
Lines 3, 8, 13 and 19, please delete "(20)".
Lines 4-5 and 27, please delete "(7 to 11)".
Line 7, please delete "(S; S')".
Line 8, please delete "(22, 23)".
Lines 12, 15 and 17, please delete "(S)".
Line 13, please delete "(22)".
Lines 14, 23 and 33, please delete "(13)".
Line 18, please delete "(23)".
Line 20, please delete "(S')".

UNITED STATES PATENT AND TRADEMARK OFFICE
CERTIFICATE OF CORRECTION

PATENT NO.   : 6,368,314 B1
DATED        : April 9, 2002
INVENTOR(S)  : Urs Kipfer It is certified that error appears in the above-identified patent and that said Letters Patent is hereby corrected as shown below:

<u>Column 12 (con't),</u>
Line 24, please delete "(V)".
Lines 26 and 28, please delete "(7)".
Line 33, please delete "(14)".
Line 35, please delete "(15)".
Lines 38, 40 and 42, please delete "(30)".
Line 39, please delete "(2)".
Lines 40 and 41, please delete "(5)".

Signed and Sealed this

Twenty-ninth Day of October, 2002

*Attest:*

*Attesting Officer*

JAMES E. ROGAN
*Director of the United States Patent and Trademark Office*